United States Patent [19]

Bosserhoff et al.

[11] Patent Number: 6,150,118
[45] Date of Patent: *Nov. 21, 2000

[54] DETECTION OF CARTILAGE DISEASES WITH MIA

[75] Inventors: Anja-Katrin Bosserhoff, Regensburg; Reinhard Büttner, Bach/Donau; Martin Kaufmann, Weilheim, all of Germany

[73] Assignee: Roche Diagnostics GmbH, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/172,877

[22] Filed: Oct. 15, 1998

Related U.S. Application Data

[60] Provisional application No. 60/062,234, Oct. 16, 1997.

[51] Int. Cl.[7] .......................... G01N 33/53; G01N 33/574; G01N 33/542; C12Q 3/00; C12Q 1/00
[52] U.S. Cl. .................................. 435/7.1; 435/3; 435/4; 435/7.23; 435/7.9; 435/7.92; 436/518; 530/388.1; 530/388.22; 530/388.8; 530/389.1
[58] Field of Search .......................... 435/7.1, 3, 4, 7.23, 435/7.9, 7.92; 436/518; 530/388.1, 388.22, 388.8, 389.1

[56] References Cited

PUBLICATIONS

Bosserhoff, et al.: Melanoma–inhibiting activity . . . : Can. Res.: 57: pp. 3149–3153, Aug. 1997.

Muller–ladner, et al.: MIA (melanoma inhibiting protein) . . . : Arth. Rheu.: 40 (9 Suppl.): 715 abstract, Sep. 1997.

*Primary Examiner*—Jeffrey Stucker
*Assistant Examiner*—Brett Nelson
*Attorney, Agent, or Firm*—Arent Fox Kintner Plotkin & Kahn, PLLC

[57] ABSTRACT

The invention concerns a method for the diagnosis and for the monitoring/screening of cartilage diseases by an MIA test, a suitable reagent for this as well as the use of antibodies to MIA to detect cartilage diseases.

12 Claims, No Drawings

DETECTION OF CARTILAGE DISEASES WITH MIA

This application claims the benefit of U.S. Provisional Application Ser. No. 60/062,234, filed Oct. 16, 1997.

The present invention concerns a method for the diagnosis of cartilage diseases by the detection of MIA, a suitable reagent therefor as well as the use of antibodies to MIA for the detection of cartilage diseases.

Cartilage diseases and in particular degenerative cartilage diseases can be attributed to different causes. These diseases of cartilage and joints are often referred to as arthritis. Arthritis forms can be classified according to the number of affected joints (monoarthritis, oligoarthritis, polyarthritis) according to their course (acute, subacute, chronic) or their cause (autoimmune, inflammatory, etc). Arthritis can for example develop due to an infection with bacteria or viruses, due to inflammatory processes in the case of diseases of the articular cartilage (arthroses), due to metabolic diseases such as gout or due to autoimmune diseases such as rheumatism (rheumatoid arthritis) or systemic lupus erythematodes. Apart from rheumatoid arthritis which is often associated with increased inflammatory parameters, osteoarthritis which usually progresses without a detectable inflammatory process is worthy of particular note.

Up to now there are only a few unspecific or costly diagnostic methods in the state of the art for the detection of cartilage diseases such as for example arthritis. For example rheumatoid arthritis is at present diagnosed on the one hand on the basis of symptoms (swollen joints, pains in the joints, immobility) and on the other hand by the detection of rheumatoid factors, detection of the classical acute phase protein CRP (C-reactive protein), detection of antinuclear antibodies (ANA) or the determination of the blood sedimentation rate (BSR). X-ray examinations or nuclear spin tomography are used as expensive physical methods.

A common feature of all the above-mentioned biochemical methods of detection and of the parameters that are to be detected is that they are generally increased in inflammations and thus non-specific. Due to the non-specificity of these tests it is not possible to differentiate between cartilage diseases, and in particular degenerative cartilage diseases, and other inflammatory and non-inflammatory diseases. The rheumatoid factor concentration is for example also increased in some patients with hepatitis, sarcoidosis and various infectious diseases and in other joint diseases such as Reiter syndrome. An increase in the concentration of CRP in the plasma or an increased blood sedimentation rate is only a general indication for an inflammatory process. An increased concentration of antinuclear antibodies only indicates the presence of an autoimmune disease.

Nowadays imaging methods are mainly used to detect osteoarthritis. Hitherto there has been no specific immuno-diagnostic test for osteoarthritis.

An immunodiagnostic method for the detection of rheumatoid arthritis by the use of antibodies to a complex of IgA and $\alpha$-1 antitrypsin is described in WO 91/19001. However, $\alpha$-1 antitrypsin often correlates with general inflammatory parameters. The complex with IgA is also mainly increased in inflammatory processes. Hence this does not enable a specific diagnosis of rheumatoid arthritis.

In EP-B 0 363 449 a specific ANA antigen of about 33 kDa is described which reacts with antibodies in samples of patients with chronic polyarthritis. The described autoantibodies are only found in some of the patients with chronic polyarthritis and also occur in some other autoimmune diseases. Moreover the titre of this autoantibody does not usually correlate with the severity of the disease.

Both cited patent applications exemplify the diagnostic problems: in the serological tests (autoantibody determination) there is a lack of sensitivity as well as of specificity and no information about the severity of the disease. The parameters and methods for the diagnosis of rheumatoid arthritis are usually approaches which correlate with the non-specific inflammation markers and thus do not have the required diagnostic specificity. The destruction of cartilage cannot be directly detected with the methods described in the state of the art.

Up to now no diagnostic method has been described in the state of the art which can be used to detect cartilage diseases and in particular degenerative cartilage diseases such as arthritis, in particular rheumatoid arthritis and osteoarthritis, in a sensitive, early, reliable and specific manner.

It was therefore the object to develop an improved diagnostic method for the detection of cartilage diseases and in particular degenerative cartilage diseases which at least partially overcomes the disadvantages of the state of the art. The method should enable a differentiation between cartilage diseases, and in particular degenerative cartilage diseases, and other diseases.

The object is achieved by the provision of a diagnostic method for the detection of a protein referred to as MIA. The method is characterized in that MIA (melanoma inhibiting activity) is detected.

MIA is a soluble protein of ca. 11 kDa in size which is secreted by malignant melanoma cells. Malignant melanoma is a malignant tumour originating from pigment-forming cells of the skin, the melanocytes, which has a strong tendency to form metastases. MIA has recently been recognized as a serum marker for malignant melanoma (Bosserhoff et al., Cancer Research 57, 1997, 3149–3153).

Surprisingly it has turned out that MIA, although it was originally described as a melanoma-associated protein, is excellently suitable as a specific marker for cartilage diseases, above all for degenerative cartilage diseases and in this case especially for arthritis. The method according to the invention is characterized in that MIA is detected. MIA is preferably detected immunologically.

It has turned out that, in comparison to the parameters of the state of the art, MIA is a considerably more specific parameter for cartilage diseases and in particular for degenerative cartilage diseases such as for example arthritis. A concentration of MIA that is increased compared to a healthy patient sample is a strong indication for the presence of arthritis.

Since MIA is a product of the chondrocytes which are cartilage cells embedded in the cartilage matrix, the concentration of MIA in arthritis-negative samples (e.g. in the case of inflammatory processes which do not occur in the cartilage) is not or hardly increased. This is a considerable advance over the state of the art. The previously known parameters are not specific for degenerative cartilage diseases and can also be increased in inflammations of another genesis or in infections.

The detection of MIA enables the direct observation of the destruction of the cartilage or of the joint.

The detection of MIA substantially avoids false positive test reactions.

The degenerative cartilage diseases that are preferably detected include rheumatoid arthritis, HLA B27 (associated arthritis) and gout. The method according to the invention has proven to be particularly suitable for the detection of rheumatoid arthritis. However, the test by the method according to the invention could also be applied to detect other cartilage and joint diseases such as for example osteoarthritis, psoriasis arthritis, systemic lupus erythematodes, systemic sclerosis or relapsing polychondritis.

The detection method according to the invention can be used in all test formats familiar to a person skilled in the art for the detection of a protein. In addition to the so-called wet tests in which the test reagents are present in a liquid phase it is also possible to use all current dry test formats that are suitable for the detection of proteins or antibodies. In these dry tests or test strips as described for example in EP-A-0 186 799 the test components are applied to a carrier. Hence no wash step is necessary if the method according to the invention is carried out in a test strip format. The method according to the invention is, however, preferably carried out as a wet test.

The test procedures which come into consideration include heterogeneous formats in which a solid phase is involved as well as homogeneous formats.

However, heterogeneous test formats are preferably used. In this case at least one receptor R1 is used which can specifically bind to the analyte MIA and is bound to a solid phase or is capable of binding to a solid phase. The sample is incubated together with R1. The solid phase can either already be present or be added at a later time. In order to detect the complex of R1 and analyte that forms, a further receptor R2 can be added which carries a label. R2 can either specifically bind to the analyte or to the receptor R1.

If R2 can specifically bind to the analyte, a sandwich complex of R1-analyte-R2 is formed which is bound to the solid phase. After separating the solid from the liquid phase, the label is determined in one of the two phases. If a sandwich method is carried out R2 is an antibody. This sandwich method is preferably used for the diagnostic MIA test for arthritis.

In the case of a sandwich test the test can be carried out as a single step i.e. all components are present simultaneously. This simplified test procedure is a major advantage particularly for screening tests in which the aim it to test numerous samples in as rapid succession as possible. Such a screening test is also a subject matter of the invention.

If R2 is a receptor that can specifically bind to R1, then R2 displaces the analyte. Thus, this is a competitive test. The label is detected in one of the two phases or in both phases after separating the solid from the liquid phase.

R1 is a receptor that can specifically bind to the analyte MIA and in addition can be bound to a solid phase. It is preferably an antibody that is capable of binding to a solid phase.

According to the invention the term "antibody" refers to monoclonal as well as polyclonal antibodies. The term "antibody" encompasses the complete antibody as well as all fragments thereof such as F(ab')2, Fab' or Fab fragments that are currently used in immunological tests and other applications. It also includes those antibodies which have been produced by modifying the antibody as long as the antigen binding property has not been significantly influenced. For example parts of the monoclonal antibodies that are normally produced in mice can be replaced by corresponding human antibody sequences by genetic engineering in order to minimize non-specific binding in the immunoassay. Processes for the production of such chimeric monoclonal antibodies are known to a person skilled in the art for example from Antibody Engineering, J. Mc Cafferty, H. R. Hoogenboom and D. H. Chiswell, The Practical Approach Series, Series Editor: B. D. Hames, Oxford University Press, 1996.

Monoclonal antibodies to MIA are particularly preferably used in the method according to the invention as a component of R1.

R1 can either be directly or indirectly bound to the solid phase. The direct binding of R1 to the solid phase is carried out by methods known to a person skilled in the art. R1 can also be bound indirectly to the solid phase by means of a specific binding system. In this case R1 is a conjugate which is composed of a receptor, preferably an antibody, and one reaction partner of a specific binding system. In this case a specific binding system is understood as two partners which can specifically react with one another. In this case the binding capability can be based on an immunological reaction or on another specific reaction. A combination of biotin and avidin or biotin and streptavidin is preferably used as the specific binding system. Other preferred combinations are biotin and antibiotin, hapten and anti-hapten, the Fc fragment of an antibody and an antibody to this Fc fragment or carbohydrate and lectin. One of the reaction partners of this specifically bindable pair is then a part of the conjugate which forms the receptor R1.

The other reaction partner of the specific binding system is present in the solid phase. The other reaction partner of the specific binding system, preferably streptavidin, can be bound to an insoluble carrier material by common methods known to a person skilled in the art. In this case a covalent as well as adsorptive binding is suitable. Particularly suitable solid phases are test tubes or microtitre plates made of polystyrene or similar plastics whose inner surface is coated with a reaction partner of the specific binding system. Particulate substances such as latex particles, molecular sieve materials, glass beads, plastic tubes etc. are also suitable and particularly preferred. Porous, laminate carriers such as paper can also be used as carriers.

R2 is composed of a receptor, which is specific for the analyte MIA or for R1, and a label. If R2 is specific for the analyte, then R2 is preferably composed of an antibody which is specific for MIA and a label. If R2 is specific for R1, then R2 is preferably composed of the analyte MIA or an analogue and a label. Monoclonal antibodies to MIA are preferably used in the method according to the invention as a component of R2.

A directly detectable substance is preferably used as a label for R2 such as a chemiluminescent, fluorescent or radioactive substance or a metal sol, latex or gold particle. Other preferred labels are enzymes or other biological molecules such as for example haptens. Digoxigenin is a particularly preferred label among the haptens. Peroxidase is one of the preferred labels among the enzymes. Labelling methods are familiar to a person skilled in the art and do not need further elucidation here. The label is detected in a well-known manner by direct measurement of the chemiluminescent, fluorescent or radioactive substance or of the metal sol, latex or gold particle or by measuring the substrate converted by the enzyme.

The label can also be detected indirectly. In this case a further receptor, which itself is in turn coupled to a signal-generating group, binds specifically to the label of R2, for example a hapten such as digoxigenin. The signal-generating group, for example a chemiluminescent, fluorescent or radioactive substance or an enzyme or gold particle is detected by methods familiar to a person skilled in the art. An antibody or an antibody fragment can for example be used as a further receptor which specifically binds to the label of R2. If this indirect detection of the label is used, the R2 label is preferably digoxigenin or another hapten and it is detected via a peroxidase-coupled antibody which is directed towards digoxigenin or towards the hapten.

All biological fluids known to a person skilled in the art can be used as samples. Body fluids such as whole blood, blood serum, blood plasma, synovial fluid (joint fluid), lymph fluid, urine, saliva etc. are preferably used as the sample.

In addition to the sample, the solid phase and the said receptors, other additives that are required for the particular application may be present in the test mixtures such as buffers, salts, detergents, protein additives such as for example BSA. The necessary additives are known to a person skilled in the art or can be found by him in a simple manner.

A further subject matter of the invention is a reagent for the detection of cartilage diseases and in particular degenerative cartilage diseases by the immunological detection of MIA which contains an MIA-specific receptor R1 that is capable of binding to a solid phase and the usual test additives for immunoassays such as buffers, salts, detergents, reducing agents such as DTT etc.

A further subject matter of the invention is a reagent for the detection of cartilage diseases and in particular degenerative cartilage diseases by immunological detection of MIA which in addition to R1 contains a receptor R2 which is specific for R1 or the analyte MIA and carries a label.

The use of antibodies to MIA for the detection of cartilage diseases and in particular degenerative cartilage diseases is also a subject matter of this invention.

The monoclonal antibodies according to the invention can be produced in a well-known manner by immunization with isolated MIA (isolated from human tissue or recombinant) in suitable experimental animals such as for example mice, rats, rabbits and subsequent fusion of the spleen cells of the immunized animals with myeloma cells. In addition to spleen cells, it is also possible to use peripheral blood lymphocytes (PBL) or lymph node cells of immunized animals (preferably mouse or rat) as the lymphocyte source.

As an alternative it is also possible to immortalize lymphocytes of human donors (tissue samples from melanoma patients) that have developed antibodies to MIA. Such anti-MIA antibody producing lymphocytes can either be immortalized by fusion with a human myeloma cell line or by Epstein-Barr-Virus (EBV) transformation to form antibody-producing hybridoma cells (Monoclonal Antibody and Immunosensor Technology, A. M. Campbell, Elsevier Publishers 1991; "Monoklonale Antikörper", J. H. Peters, H. Baumgarten, Springer Publishers 1990; Monoclonal Antibody Production Techniques and Applications, ed. Lawrence B. Schook, Marcel Dekker Publishers 1987).

The invention is elucidated further by the following example.

EXAMPLE 1

ELISA test for the detection of MIA for the diagnosis of cartilage diseases

Incubation buffer for the MIA-ELISA (weights stated per liter):

| | | |
|---|---|---|
| NaH$_2$PO$_4$ | 0.97 g | |
| Na$_2$HPO$_4$ | 5.88 g | |
| di-Na tartrate | 46 g | |
| synperonic F 68 | 5 g | |
| bovine IgG | 1 g | |
| bovine albumin | 2 g; | the pH value is adjusted to 7.4 with NaOH. |

Procedure:

10 μl standard solution (rec.h-MIA in 50 mmol/l HEPES, 150 mmol/l NaCl, pH 7.0, 2% w/v BSA; dilution series containing 0, 3.13, 6.25, 12.5, 25, 50 ng/ml) or 10 μl of the sample to be determined (serum, plasma etc.) is placed in the wells of a microtitre plate coated with streptavidin (Boehringer Mannheim GmbH, Cat. No. 1 664 778). Subsequently 200 μl of a solution of 1 μg/ml MAB<MIA>M-2F7-Bi and 25 mU/ml MAB<MIA>M-1A10-POD in incubation buffer is pipetted into each well containing the standard or sample. The microtitre plate is then shaken at 500 rpm for 45 minutes at room temperature (20–25° C.) on a commercial shaker for microtitre plates (e.g. IKA MTS 4).

The wells of the microtitre plate are carefully emptied and washed three times with 300 μl washing solution (250 mg NaCl/l, 1 mg CuSO$_4$/l, Boehringer Mannheim GmbH, Cat. No. 1 059 475) each time.

200 μl ABTS® substrate solution (2,2'-azino-di[3-ethyl-benzthiazoline-sulfonate] 1.9 mmol/l ABTS®, 100 mmol/l phosphate-citrate buffer, pH 4.4, sodium perborate 3.2 mmol/l) is pipetted into each of the coated wells of the microtitre plate and incubated for 30 minutes at room temperature (20–25° C.) on the plate shaker at 500 rpm.

The absorbance values of the resulting colour solutions in the wells are measured at 405 nm with a suitable photometer for microtitre plates. A standard curve is established from the signals and the concentration values of the standard series from which the sample concentrations can be read off.

The ELISA test procedure described here was used to determine the MIA concentrations in the serum of patients with rheumatoid arthritis (RA), HLA B27-associated oligoarthritis (HLA B27), gout and of healthy normal patients (NP).

The results are shown in Table 1.

TABLE 1

| Type of samples | Number of tested samples | Percentage of samples with increased MIA concentration | Average MIA concentration in ng/ml |
|---|---|---|---|
| Normal patients | 100 | 0 | 0–4; cut-off: 6.5 |
| RA | 46 | 24/46 = 52% | 12.3 |
| HLA B27 | 12 | 6/12 = 50% | 6.6 |
| gout | 10 | 4/10 = 40% | 6.6 |

It can be seen that increased MIA serum concentrations can be found in patients with degenerative cartilage diseases that are associated with joint destruction. The MIA concentration is considerably increased particularly when rheumatoid arthritis (RA) is present. An MIA concentration of 6.5 ng/ml was determined as the cut-off value.

The highest MIA concentrations were associated with positive results for rheumatoid factors. However, the highest MIA concentrations did not correlate with an increased blood sedimentation rate or increased CRP-concentration.

This shows that MIA is suitable as a diagnostic marker for cartilage diseases and above all degenerative cartilage disease, in particular rheumatoid arthritis.

Incorporated by reference herein is copending United States patent application to Kaluza et al, U.S. Ser. No. 08/993,092, filed on Dec. 18, 1997, now U.S. Pat. No. 5,973,123.

What is claimed is:

1. A method of detecting cartilage disease, comprising incubating a sample containing an analyte with an immunological reagent that binds native melanoma inhibiting activity protein to form a complex of the analyte and the reagent and detecting said complex as an indication of the presence of cartilage disease, wherein detecting melanoma inhibiting activity protein at a level of 6.5 ng/ml or above is indication of disease.

2. The method according to claim 1 wherein said immunological reagent is at least one antibody that binds native melanoma inhibiting activity protein.

3. The method according to claim 2 wherein said at least one antibody comprises a monoclonal antibody that binds native melanoma inhibiting activity protein.

4. The method according to claim 1 wherein said immunological reagent includes a antibody that binds native melanoma inhibiting activity protein and that binds to a solid phase.

5. The method according to claim 4, further including a antibody having a label and binding at least one of said antibody that binds native melanoma inhibiting activity protein and a melanoma inhibiting activity protein analyte.

6. The method according to claim 4 wherein said analyte is detected using a sandwich test.

7. The method according to claim 1 wherein said analyte is detected using an ELISA test.

8. The method according to claim 1 wherein said immunological test reagent is applied to a test strip.

9. The method according to claim 1 wherein the disease detected is a degenerative cartilage disease.

10. The method according to claim 1 wherein the disease detected is arthritis.

11. The method according to claim 1 wherein the disease detected is rheumatoid arthritis, osteoarthritis, psoriases arthritis, HLA B27, gout, systemic scleroses, systemic lupus erythematodes or relapsing polychondritis.

12. The method according to claim 10 wherein the disease detected is rheumatoid arthritis.

* * * * *